United States Patent
Itzel

(10) Patent No.: US 7,318,809 B2
(45) Date of Patent: Jan. 15, 2008

(54) METHOD FOR MONITORING A CHILDBIRTH PROCESS

(76) Inventor: Eva Itzel, Ridvagen 14, 182 39 Danderyd (SE)

( * ) Notice: Subject to any disclaimer, the term of this patent is extended or adjusted under 35 U.S.C. 154(b) by 208 days.

(21) Appl. No.: 10/564,412

(22) PCT Filed: Aug. 18, 2004

(86) PCT No.: PCT/US2004/026888

§ 371 (c)(1),
(2), (4) Date: Jan. 11, 2006

(87) PCT Pub. No.: WO2005/034762

PCT Pub. Date: Apr. 21, 2005

(65) Prior Publication Data

US 2006/0180161 A1    Aug. 17, 2006

Related U.S. Application Data

(60) Provisional application No. 60/481,376, filed on Sep. 15, 2003.

(51) Int. Cl.
*A61B 5/117* (2006.01)
*A61B 5/103* (2006.01)

(52) U.S. Cl. .................................................... 600/588

(58) Field of Classification Search ................ 600/513, 600/438, 347, 588, 309, 551, 310, 322, 300, 600/520; 482/900, 5, 8; 514/557, 558
See application file for complete search history.

(56) References Cited

U.S. PATENT DOCUMENTS

| | | | | |
|---|---|---|---|---|
| 5,119,819 | A * | 6/1992 | Thomas et al. | 600/438 |
| 6,103,764 | A * | 8/2000 | Nissen | 514/557 |
| 6,411,841 | B2 * | 6/2002 | Heikkila | 600/513 |
| 6,736,759 | B1 * | 5/2004 | Stubbs et al. | 482/8 |

* cited by examiner

*Primary Examiner*—Max Hindenburg
*Assistant Examiner*—Brian Szmal
(74) *Attorney, Agent, or Firm*—Rolf Fasth; Fasth Law Offices

(57) ABSTRACT

The method is for monitoring a childbirth process of a pregnant woman. In a measuring step, a lactate concentration of vaginal fluids is measured. In a comparison step, it is determined if the measured lactate concentration is greater than a predetermined lactate concentration that indicates that amniotic fluid has passed from an amnion of the pregnant woman. In a measuring step, the lactate concentration is measured. In a comparison step, it is determined if the measured lactate concentration is greater than a lactate threshold interval. When the lactate concentration is less than the lactate threshold interval the pregnant woman is stimulated in a stimulating step to give birth.

10 Claims, 1 Drawing Sheet

METHOD FOR MONITORING A CHILDBIRTH PROCESS

This application is a U.S. national phase application based on International Application No. PCT/US2004/026888 filed 18 Aug, 2004, claiming priority from U.S. Provisional Patent Application No. 60/481,376 filed 15 Sep. 2003.

TECHNICAL FIELD

The present invention relates to a method for monitoring a childbirth process of a pregnant woman.

BACKGROUND OF THE INVENTION

One problem in today's delivery methods is that women suffer from dystocya during labor. This could result in that the delivery does not progress as desired and that the labor is drawn out without a successful natural childbirth. The pregnant woman may become frustrated and it may be necessary to use methods such as, vacuum, forceps or caesarean to deliver the baby. The dystocya of the pregnant woman may also expose the fetus to injury and fatigue.

The lactate concentration in the blood of the fetus has been measured in the past to control that the fetus does not suffer from oxygen deficiency. However, the lactate concentration in the fetus does not indicate the condition of the pregnant woman. There is a need to more effectively determine and control the condition of woman suffering from dystocya at an early stage to avoid unnecessary labor before using surgical and alternative childbirth methods.

SUMMARY OF THE INVENTION

The method of the present invention provides a solution to the above-outlined problems. More particularly, the method is for monitoring a childbirth process of a pregnant woman. In a first measuring step, a first lactate concentration of vaginal fluids is measured. In a comparison step, it is determined if the measured lactate concentration is greater than a predetermined lactate concentration value that indicates that amniotic fluid has passed from amnion of the pregnant woman and the membrane has ruptured. In a second measuring step, a second lactate concentration is measured. In a second comparison step, it is determined if the measured second lactate concentration is greater than a lactate threshold interval. When the second lactate concentration is less than the lactate threshold interval the pregnant woman is stimulated in a stimulating step to give birth. When the second lactate concentration is greater than the lactate threshold interval and labor does not progress normally, the woman may be subjected to alternative childbirth options such as a surgical childbirth, to prevent unnecessary agonizing and drawn out efforts to give birth.

DETAILED DESCRIPTION

Figure 1:
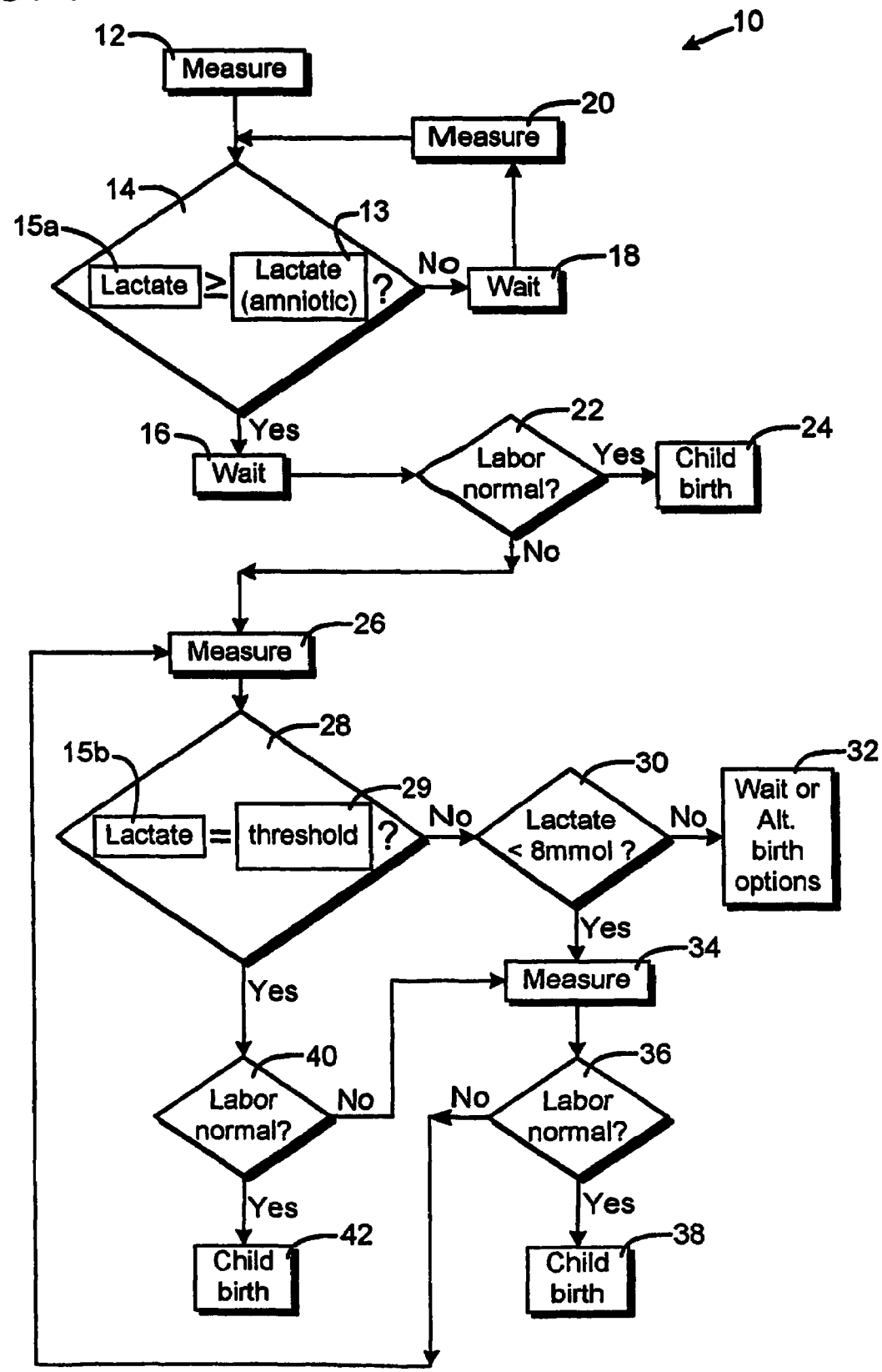
FIG. 1 is a schematic flow chart showing some of the steps of the method of the present invention.

With reference to FIG. 1, the method 10 of the present invention includes a measuring step 12 that measures a lactate concentration 15$a$ in fluids, such as vaginal fluids, in connection with pregnancy to determine whether the amniotic fluids have passed or are in the process of being passed from the amnion. In general, the uterus muscle of pregnant women produces lactate so that the lactate concentration of the vaginal fluids may be measured to provide a measurement of the amount of lactate produced by the uterus muscle. Non-pregnant women often have no or very little lactate in the vaginal fluids.

If the lactate concentration 15$a$ is higher than a predetermined lactate concentration 13, such as 4-5 mmol/l, more preferably higher than 4.5 mmol/l, as indicated in a comparison step 14 then it may be concluded that the membranes have ruptured and amniotic fluids likely have passed and that the childbirth labor is likely to start after a waiting period 16. It is to be understood that the 4-5 mmol/l is an illustrative example that applies to most women and that the invention is not limited to the values used in the examples.

If the lactate concentration is lower than 4.5 mmol/l then there is a high likelihood that the amniotic fluids are still contained within the amnion. The lactate concentration may again be measured in a measuring step 20 after a waiting period 18. It is again determined in the comparison step 14 whether the lactate concentration is more or less than 4.5 mmol/l. If the lactate concentration is again below 4.5 mmol/l, a second measuring may be conducted later and the measuring may be repeated at suitable time intervals until the lactate concentration exceeds 4.5 mmol/l or it is obvious that the amniotic fluids have passed.

As indicated above, if the lactate concentration measured in the measuring step 12 is above 4.5 mmol/l, the next step is to wait for about two days or so to see if the woman starts the labor by herself. In a determining step 22, it is determined whether the labor has started or not. If the labor has started and is progressing normally then the childbirth procedure 24 may proceed. If it is determined in the determining step 22 that the labor has not started or the labor is not progressing normally, a lactate concentration 15$b$ is measured in a measuring step 26.

In a comparison step 28 it is then determined if the lactate concentration 15$b$ as measured in the measuring step 26 is within a lactate threshold interval 29 that may be about 8-10 mmol/l. If the lactate concentration as measured in the step 26 is not within the threshold interval 29, then it is determined in a comparison step 30 whether the lactate concentration is less than the threshold interval 29 or about 8 mmol/l. If the lactate concentration as measured in step 26 is greater than the threshold interval 29 then a waiting step 32, such as a couple of hours, may start to see if the labor progress normally. If labor does not progress normally, alternative childbirth options may be considered such as caesarean, forceps or the use of suction cups that are connected to vacuum to draw out the baby. An important feature of the present invention is that the monitoring of the lactate concentration may be used to predict whether the woman is likely to give a natural birth or not without forcing the pregnant woman to go through long and agonizing efforts to give birth. It is therefore possible to use alternative childbirth options at a relatively early stage. It is to be understood that the 8-10 mmol/l is an illustrative example that applies to most women and that the invention is not limited to the values used in the examples.

If the lactate concentration, as measured in step 26, is less than the threshold interval 29, then the woman may be stimulated with drugs or other aids to give birth in a stimulation step 34. In a determining step 36, it may be determined if the labor is progressing normally. If the labor is progressing normally the woman may proceed to give birth 38. If the labor is not progressing normally, the lactate concentration may again be measured in the measuring step 26 and the process continues in the comparison step 28, as described above.

If it is determined in the comparison step 28 that the lactate concentration, as measured in step 26, is at the threshold interval 29, such as between 8-10 mmol/l, then it is determined whether the labor is progressing normally in a determining step 40. If labor is progressing normally, the woman may proceed to give birth 42. If labor is not progressing normally, the woman may be stimulated to give birth in the stimulation step 34 and the process continues to the determining step 36, as described above.

The various processing loops may continue until the woman either gives birth by herself or is subjected to alternative childbirth options. As indicated above, an important feature of the present invention is that the woman may be prevented from agonizing and long childbirth efforts before alternative childbirth options are used. Alternative childbirth options may be used at an earlier stage when the lactate concentration indicates that the uterus muscle is operating above the lactate threshold without resulting in a natural childbirth.

While the present invention has been described in accordance with preferred compositions and embodiments, it is to be understood that certain substitutions and alterations may be made thereto without departing from the spirit and scope of the following claims.

The invention claimed is:

1. A method of monitoring a childbirth process of a pregnant woman, comprising:
   measuring a lactate concentration;
   determining whether the measured lactate concentration is greater than a lactate threshold interval; and
   subjecting the pregnant woman to alternative child birth options when the lactate concentration is greater than the lactate threshold interval.

2. The method according to claim 1 wherein the method further comprises determining whether labor is progressing normally.

3. The method according to claim 2 wherein the method further comprises measuring the lactate concentration when labor, has not started or is not progressing normally.

4. The method according to claim 3 wherein the method further comprises stimulating the pregnant woman to give birth when the lactate concentration is less than the lactate threshold interval.

5. The method according to claim 4 wherein the method further comprises determining whether labor is progressing normally.

6. The method according to claim 5 wherein the method further comprises measuring the lactate concentration when the labor is not progressing normally.

7. The method according to claim 1 wherein the method further comprises determining whether labor is progressing normally when the lactate concentration is within the lactate threshold interval and providing stimulation to the pregnant woman when that the labor is not normal.

8. The method according to claim 1 wherein the method further comprises measuring a lactate concentration in vaginal fluids; determining whether the measured lactate concentration is greater than a predetermined lactate concentration that indicates that the membrane has ruptured and amniotic fluid has passed from an amnion of the pregnant woman.

9. The method according to claim 8 wherein the method further comprises waiting when the lactate concentration is less than the predetermined lactate concentration and again measuring the lactate concentration.

10. The method according to claim 9 wherein the method further comprises waiting when the lactate concentration is greater than the lactate concentration.

* * * * *